(12) United States Patent
Marcy et al.

(10) Patent No.: US 12,275,009 B2
(45) Date of Patent: *Apr. 15, 2025

(54) MICROFLUIDIC CARTRIDGE

(71) Applicant: Gen-Probe Incorporated, San Diego, CA (US)

(72) Inventors: Yann Marcy, Marseilles (FR); Marc Artigue, Noisy Sur Ecole (FR); Quentin Le Masne, Grenoble (FR); Kevin Marq, Boulogne-Billancourt (FR)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/482,796

(22) Filed: Oct. 6, 2023

(65) Prior Publication Data

US 2024/0131511 A1 Apr. 25, 2024
US 2024/0226883 A9 Jul. 11, 2024

Related U.S. Application Data

(63) Continuation of application No. 16/845,631, filed on Apr. 10, 2020, now Pat. No. 11,813,609, which is a
(Continued)

(30) Foreign Application Priority Data

Nov. 29, 2013 (EP) .................................. 13306643

(51) Int. Cl.
*B01L 3/00* (2006.01)
*B01L 9/00* (2006.01)
*C12Q 1/6844* (2018.01)

(52) U.S. Cl.
CPC ..... *B01L 3/502715* (2013.01); *B01L 3/50273* (2013.01); *B01L 3/502738* (2013.01);
(Continued)

(58) Field of Classification Search
CPC . B01L 3/50273; B01L 3/502738; B01L 9/527
See application file for complete search history.

(56) References Cited

U.S. PATENT DOCUMENTS 4,522,622 A 6/1985 Peery et al.
10,654,039 B2 5/2020 Marcy et al.
(Continued)

OTHER PUBLICATIONS

Office Action issued in Australian Patent Application No. 2014356426 dated Feb. 21, 2019.

*Primary Examiner* — Natalia Levkovich
(74) *Attorney, Agent, or Firm* — Richard Wydeven, Rothwell, Figg, Ernst & Manbeck, P.C.; Charles B. Cappellari

(57) ABSTRACT

A microfluidic cartridge for detecting one nucleic acid of a sample, including a plurality of functional volumes split into functional areas and a fluidic network of microchannels. At least three functional areas are fluidly connected to a central distribution hub of fluids by one or more hub-connected microchannels, the central distribution hub being capable of pumping and injecting fluids from a first functional area to a second functional area by passing through the central distribution hub; and at least three valves of hub-connected microchannels are arranged so that the at least three valves are adapted to be actuated mechanically by a single external cam-driven actuator.

20 Claims, 7 Drawing Sheets

Related U.S. Application Data continuation of application No. 15/039,860, filed as application No. PCT/EP2014/075868 on Nov. 27, 2014, now Pat. No. 10,654,039.

(52) U.S. Cl.
CPC ............ *B01L 9/527* (2013.01); *C12Q 1/6844* (2013.01); *B01L 2200/027* (2013.01); *B01L 2200/16* (2013.01); *B01L 2300/0654* (2013.01); *B01L 2300/0819* (2013.01); *B01L 2300/0848* (2013.01); *B01L 2300/0864* (2013.01); *B01L 2300/087* (2013.01); *B01L 2300/0887* (2013.01); *B01L 2400/0478* (2013.01); *B01L 2400/0487* (2013.01); *B01L 2400/0622* (2013.01); *B01L 2400/0638* (2013.01); *B01L 2400/0644* (2013.01); *B01L 2400/065* (2013.01); *B01L 2400/0655* (2013.01)

(56) References Cited

U.S. PATENT DOCUMENTS

| | | |
|---|---|---|
| 11,813,609 B2 | 11/2023 | Marcy et al. |
| 2024/0131511 A1 | 4/2024 | Marcy et al. |

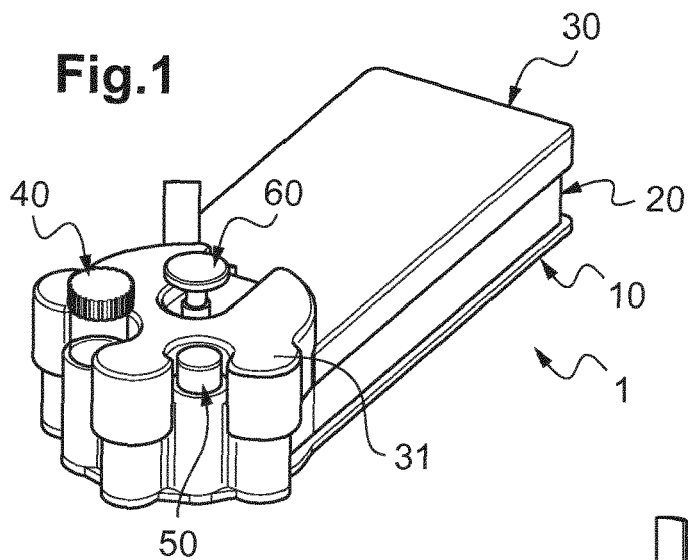
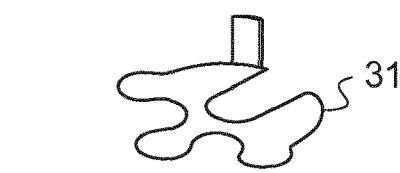
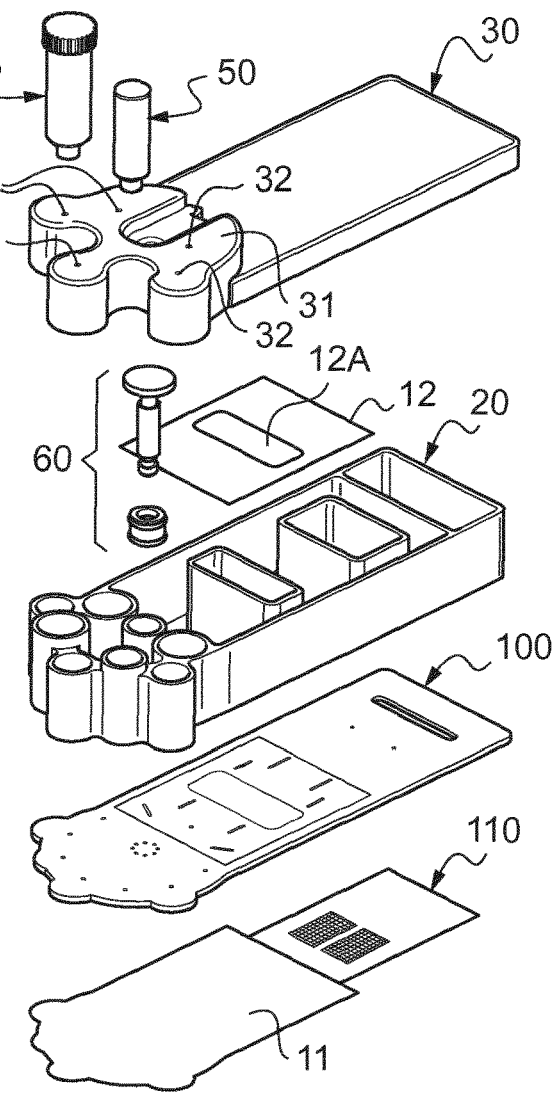

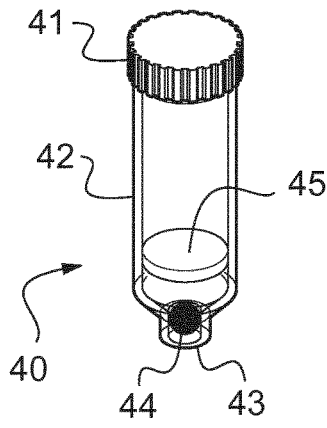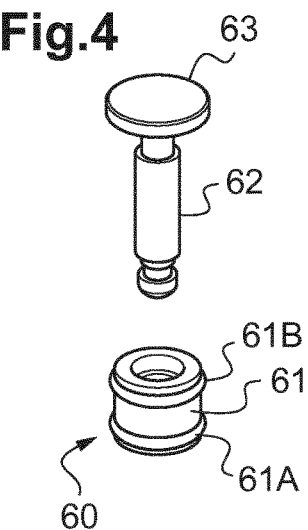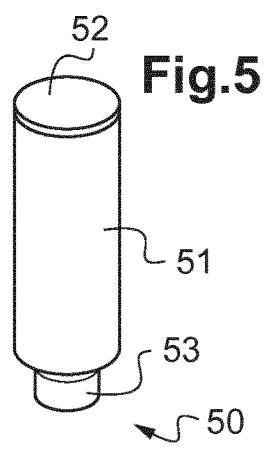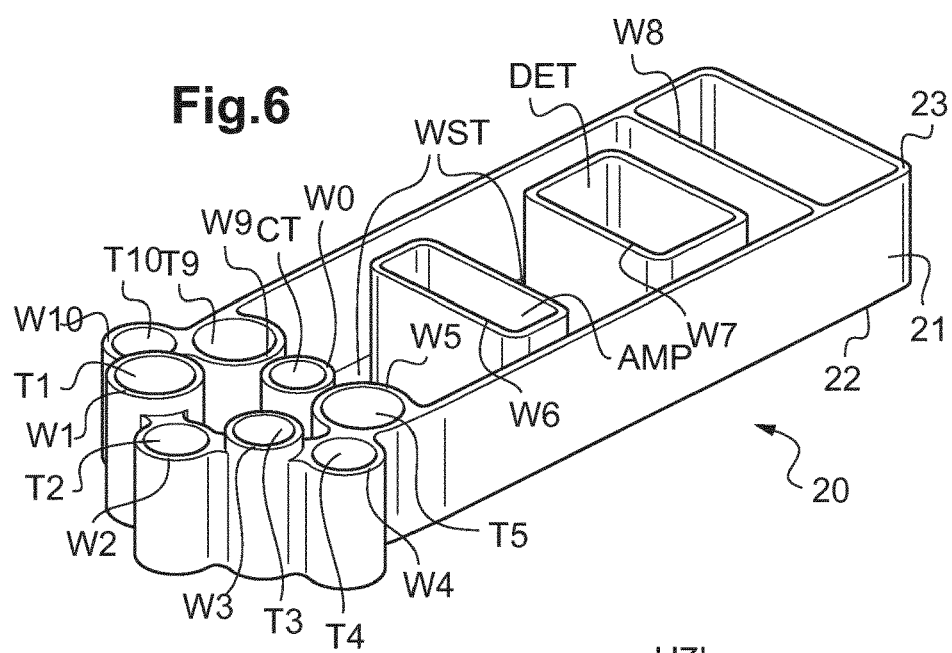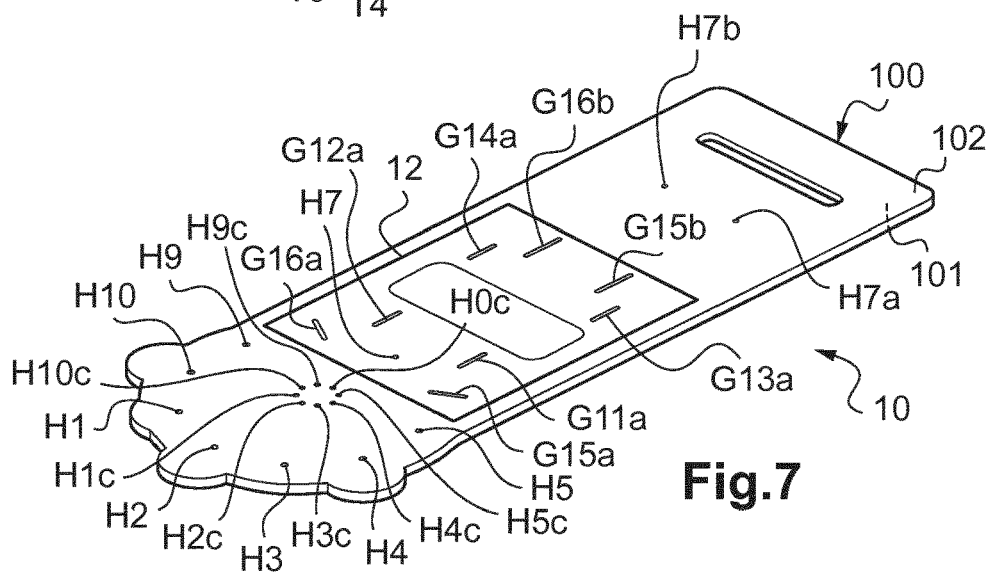

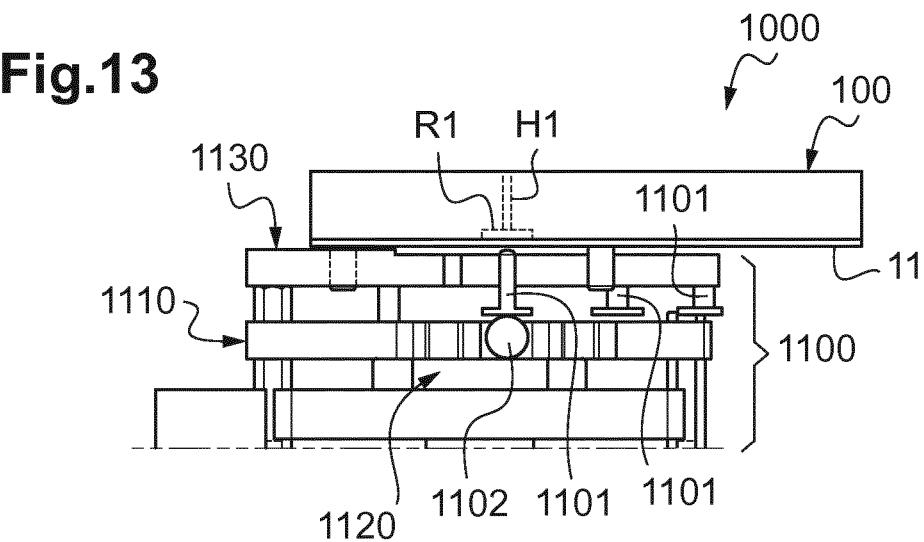
Fig.13
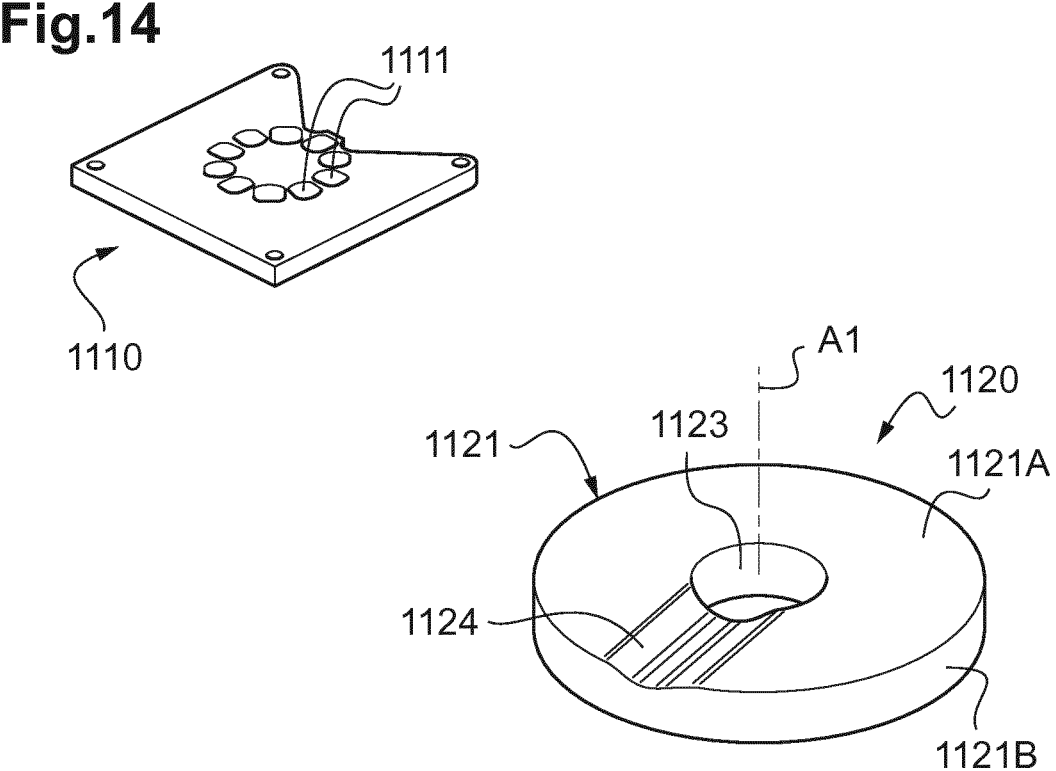
Fig.14
Fig.15

MICROFLUIDIC CARTRIDGE

CROSS-REFERENCE TO RELATED APPLICATIONS

This application is a continuation of U.S. application Ser. No. 16/845,631, filed Apr. 10, 2020, now U.S. Pat. No. 11,813,609, which is a continuation of U.S. application Ser. No. 15/039,860, filed May 27, 2016, now U.S. Pat. No. 10,654,039, which is a '371 of International Application No. PCT/EP2014/075868, filed Nov. 27, 2014, which claims the benefit of EP Application No. 13306643.1, filed Nov. 29, 2013, the contents of each of which applications is hereby incorporated by reference herein in its entirety.

BACKGROUND

The invention relates to the field of microfluidic devices used to make molecular or biological diagnostics.

The invention more particularly relates to a microfluidic cartridge for analyzing at least one nucleic acid contained in a biological sample.

The invention also relates to a docking station designed to use and operate such a microfluidic cartridge.

The invention finally relates to a method of analysis of a biological sample implementing such a microfluidic cartridge.

DESCRIPTION OF THE RELATED ART

Microfluidic devices designed for the search and the analysis of at least one nucleic acid or one nucleotide sequence contained in a biological sample incorporate various means in order to: prepare the biological sample to extract nucleic acids from said sample; amplify the at least one target nucleic acid from the extracted nucleic acids using standard amplification techniques like, for example, Polymerase Chain Reaction (also known as «PCR»); and detect, e.g. optically, and analyze the target nucleic acids using known molecular recognition mechanisms like, for example, hybridization.

Therefore, in order to perform the analysis of the at least one nucleic of a sample, said sample needs to be transferred sequentially in different functional areas of the micro microfluidic cartridge, each functional area being dedicated to a specific operation on the sample.

The documents WO 2009/049268 and US 2012/115738 describe, for example, a microfluidic device comprising a plurality of functional areas: an area of sample preparation for extraction of nucleic acids, a range of nucleic acid amplification, and a surface analysis and detection of amplified nucleic acids. Said detection area is likely to be a biochip.

In those documents, the microfluidic cartridge features very complex structure so as to be modular and allow an easy and rapid reconfiguration in order to suit various applications. In particular, many pumps with shared-valve structure are implemented within each of the functional areas of the microfluidic cartridge to transfer fluids from one functional area to the other.

Therefore, the cartridge of documents WO 2009/049268 and US 2012/115738 presents a large volume and the transfer of fluids cannot be operated in a simple manner, with a limited number of actuators.

The widespread use of these devices, especially in the context of molecular diagnostics in humans, for which the cartridge must be discarded after each use, is limited by the complexity and high costs inherent in this technology. Furthermore, these devices, such as the one described in US 2012/0034705, often consisting of a variety of many elements for achieving the various stages of analysis, they are extremely fragile and difficult to handle.

It is therefore desired that a microfluidic cartridge is mass producible, inexpensive, and most preferably disposable. However, because such microfluidic devices integrate complex steps of molecular analysis, it may be difficult to properly coordinate various tasks of conventional microfluidic devices. It is therefore also desired that the microfluidic cartridge be simple to operate and that many or substantially all of the fluid processing steps be automated directly on the microfluidic cartridge.

For that purpose, the present invention proposes a microfluidic cartridge making it possible, on the one hand, to integrate, within the latter, not only all the fluids required for its operation, but also the whole of microfluidic circuits, microchannels and valves, the reaction chamber and the biochip, and, on the other hand, to make transfers and movements of fluids in a simple manner, in a reduced volume and by means of a compact external actuator.

More precisely, the present invention provides a microfluidic cartridge for detecting at least one nucleic acid of a sample, said microfluidic cartridge comprising:
  a plurality of functional volumes split into functional areas such as at least, a sample preparation area, a nucleic acid amplification area, a nucleic acid analysis area, a waste area, and
  a fluidic network of microchannels,
  wherein:
  at least three functional areas are fluidly connected to one central distribution hub of fluids distribution by one or more hub-connected microchannels, each of said hub connected microchannels having a hub end and an area end, said central distribution hub being capable of pumping and injecting fluids from a first functional area to a second functional area of said at least three functional areas by passing through said central distribution hub, said second functional area being identical or different from said first functional area, and
  at least three valves, each located on a hub-connected microchannel, are arranged in said microfluidic cartridge so that said at least three valves are adapted to be actuated mechanically by a single external cam-driven actuator.

The microfluidic cartridge according to the invention has thus the advantage, thanks to the use of the central distribution hub of fluids, to facilitate the transfers of fluid from a first functional area to a second functional area. This makes it possible to use only one simple fluid displacement system (typically a pumping system) for most of the fluid movements of the microfluidic cartridge, for inducing depressurization and pressurization in order to displace the fluid from a functional volume or area to another one and to reduce the volume of the microfluidic cartridge.

The microfluidic cartridge comprises less moving elements and its cost is therefore reduced compared to prior-art cartridges.

Moreover, the system for actuation of the valves of the microchannels connected to the central hub may also be more compact and simpler than the system disclosed in US 2012/0034705, thanks to the arrangement of these valves in the microfluidic cartridge.

In one embodiment, the at least three functional areas that are connected to the central distribution hub are the sample preparation area and the waste area.

In one embodiment, the at least three functional areas comprise the nucleic acid analysis area, and/or the nucleic acid amplification area.

In another embodiment, the at least three functional areas comprise the sample preparation area, the nucleic acid analysis area, and the waste area.

In another embodiment, the at least three functional areas comprise all functional areas of the microfluidic cartridge.

In one embodiment, the microfluidic cartridge further comprises at least two valves that are actuated by linear actuators and are independent of the cam-driven actuator.

The microfluidic cartridge according to the present invention may be seen as a "lab-on-a-chip" that can perform the complete nucleic acid analysis of a sample, from sample collection to the reading of the result, typically performed in the diagnostics or microbiology laboratory.

The detection of the presence in the sample, of a nucleic acid or molecular marker whose sequence is specific to a gene of interest, is understood as a molecular diagnostics in this application.

The microfluidic cartridge integrates usually over a few square centimeters several specialized functional areas and volumes performing complex analysis conventionally made using several laboratory apparatus. The advantages are that theses operations can be automated while consuming low reagents volumes.

Besides, other advantageous and non-limiting characteristics of the microfluidic cartridge according to the invention are described below. The said characteristics correspond to various embodiments of the invention that can be taken alone or in combination.

The at least three valves are spatially arranged in the microfluidic cartridge so that they are adapted to be actuated simultaneously by the single external cam-driven actuator. In particular embodiments of the invention, said at least three valves are linearly or circularly arranged in the microfluidic cartridge.

Typically, the said at least three valves are valves of hub-connected microchannels, connecting the sample preparation area, the nucleic acid analysis area, and the waste area to the central hub. Preferentially, the said valves are located close to, or at the area end of the said hub-connected microchannels, said area end being the one of the two ends of the hub-connected microchannel which is turned towards the corresponding functional area. On the opposite, the hub end is the one of the two ends of the hub-connected microchannel which is turned towards the central distribution hub of fluids.

In one embodiment of the invention, each hub microchannel comprises one valve located, close to, or at their area end. Said valves are preferentially spatially arranged in order to be simultaneously actuated by the external cam-driven actuator as mentioned above.

At least two functional areas of the plurality of functional areas can also be directly fluidly connected to each other by one or more area-connecting microchannels, each of the said area-connecting microchannels having at least a valve that is preferentially actuated by a linear actuator independent of the cam-driven actuator.

For example, said two functional areas are the nucleic acid amplification area and the nucleic acid analysis area.

In another example, the said two functional areas are the nucleic acid analysis area and the waste area.

Typically, a microfluidic cartridge according to the invention is disposable and comprises:

a cartridge plate comprising:
  a substrate having a first face and a second face, a plurality of grooves flush with the first or second surface and a plurality of through holes connecting said first and second surfaces, and
  a first film bonded on first face of said substrate of the cartridge plate, said grooves flush with the first face being sealed by said first film to form the hub-connected microchannels, said first film being a first deformable membrane adapted to be deformed by an external actuator,
a cartridge body in contact with the cartridge plate on the second surface of said substrate, said cartridge body comprising:
  a lateral wall which extends from the second surface of said substrate, and
  a plurality of internal walls which defines a plurality of functional volumes of said cartridge body, and
  a cartridge cover adapted to close the different functional volumes.

In one embodiment, the cartridge plate comprises a second film bonded on the second face of the substrate of the cartridge plate, the plurality of grooves flush with the second face being sealed by said second film to form the area-connected microchannels.

Typically, the cartridge plate comprises at least one recessed cavity formed in the substrate and extending from the first face.

Typically also, the first film bonded on the first face of the substrate closes said at least one recessed cavity to form at least one reactive chamber for nucleic acid amplification.

In a preferred embodiment, a micro-array slide (or biochip) bonded on the first face of the substrate closes said at least one recessed cavity to form at least one detection chamber for nucleic acid analysis.

In a preferred embodiment, the microfluidic cartridge comprises a semi-permeable membrane between the cartridge body and the cartridge cover adapted to let air pass through it while preventing liquids to leak out of the functional volumes.

Typically, the functional volumes of the cartridge body encompass several functional areas (e.g.: at least a sample preparation area, a nucleic acid amplification area, a nucleic acid analysis area and a waste area). Said functional volumes are containers adapted to receive tubes, fluids such as sample, reagent products, or a purification column.

In one embodiment, the central hub of fluid distribution comprises a hub body and a plunger seal adapted to slide in and out of the hub body to pump from or inject fluids in the functional areas of said microfluidic cartridge through the hub-connected microchannels.

In another embodiment, the central hub of fluid distribution comprises also a syringe having a plunger to which the plunger seal is attached.

The microfluidic cartridge is adapted to be inserted into a docking station, within equipment designed to perform at least the following functions: thermal control, control of fluid flow, valves actuation and optical detection.

The present invention also proposes a docking station intended to use and operate a microfluidic cartridge such as mentioned above.

Therefore, the present invention provides a docking station adapted to receive a microfluidic cartridge according to the invention, comprising:
  a cam-driven actuator adapted to simultaneously actuate the at least three valves of hub-connected microchannels, means for optical excitation of the micro-array slide of said cartridge, and means for optical detection of an optical signal that is representative of said nucleic acid in the sample analyzed by the cartridge.

In one embodiment, the docking station also comprises actuation means adapted to actuate linear/independently actuated valves of said microfluidic cartridge.

In a particular embodiment, the cam-driven actuator is a rotational-motion actuator.

In another particular embodiment, the cam-driven actuator is a linear-motion actuator.

Preferentially, the cam-driven actuator of the docking station is designed to open, among the valves of the microchannels connected to the central hub, at most only one of said valves.

In a preferred embodiment, the docking station according to the invention comprises sliding means adapted to slide the syringe of the central hub in and out of the hub body to pump from or inject fluids in the functional areas of said microfluidic cartridge through the hub-connected microchannels.

It is also an object of the present invention to provide an apparatus for analyzing a biological sample comprising such docking station and microfluidic cartridge according to the present invention, for analyzing at least a nucleic acid of a sample.

Furthermore, the microfluidic cartridge according to the invention is particularly adapted to be used in a process for analyzing a biological sample.

Therefore, it is another object of the present invention to propose a process for analyzing a biological sample, comprising the steps of:

a. providing said biological sample into at least one functional volume of a sample preparation area of a microfluidic cartridge according to the invention, b. allowing said biological sample to get into contact with at least one reagent and/or one purification column present in another functional volume of the sample preparation area by actuating at least one valve controlling the flow of fluids of microchannels, c. recovering the product resulting of step b to obtain an isolated DNA sample, d. transferring the isolated DNA sample to at least one functional volume of the nucleic acid amplification area, e. allowing said isolated DNA sample to get into contact with at least a reagent for amplification and closing the valves of the functional volume of the amplification area, f. performing DNA amplification, g. recovering amplified DNA obtained at step f) and transferring it to another functional volume of the hybridization area by actuating at least one valve controlling the flow of fluids of microchannels, h. allowing said amplified DNA to get into contact with at least one compound capable of hybridizing with said DNA in the hybridization chamber, and i. obtaining a microarray image and automatically analyzing it.

BRIEF DESCRIPTION OF THE DRAWINGS

An embodiment of the invention will now be described in detail with reference to the drawings, in which:

FIG. 1 is a perspective view of a microfluidic cartridge in a preferred embodiment of the invention;

FIG. 2 is an exploded view of the microfluidic cartridge of FIG. 1, making appear the cartridge plate, the cartridge body and the cartridge cover;

FIG. 3 is a schematic view of a preparation tube for a biological sample to analyze with the microfluidic cartridge of FIG. 1;

FIG. 4 is an exploded schematic view of a syringe that can be used in the microfluidic cartridge of FIG. 1 to pump and inject the fluids;

FIG. 5 is a schematic view of an «amplification mix» tube to be inserted in the microfluidic cartridge of FIG. 1;

FIG. 6 is a detailed view of the cartridge body of FIG. 2;

FIG. 7 is a detailed view of the cartridge plate of FIG. 2;

FIG. 13 is a schematic view of a rotational-motion cam-driven actuator using balls to actuate the valves of the microfluidic cartridge;

FIG. 14 is a schematic view of a perforated actuator plate allowing the holding in place of the balls of the cam-driven actuator of FIG. 13;

FIG. 15 is a schematic view of a circular plate having a detent operating in the mechanism of the cam-driven actuator of FIG. 13;

DETAILED DESCRIPTION OF THE PREFERRED EMBODIMENTS

Figure 8:
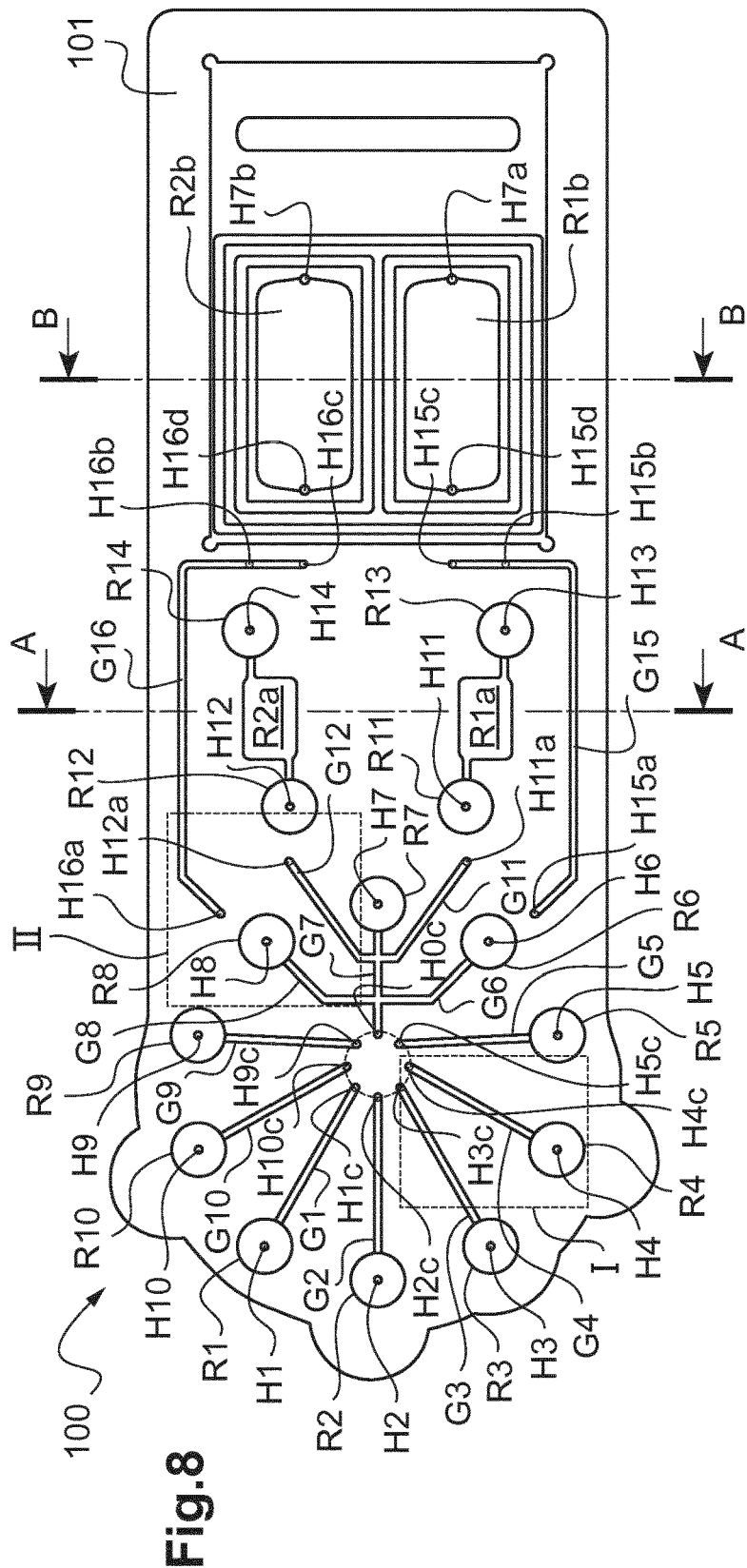
FIG. 8 is a bottom view of the cartridge plate of FIG. 7.

It has been shown in FIG. 1 and FIG. 2, respectively, an assembled view and an exploded view of a microfluidic cartridge 1 according to a preferred embodiment of the invention, in which the microfluidic cartridge 1 is herein a disposable cartridge. It is meant by this that the microfluidic cartridge 1 is intended to be disposed of and placed in a container intended for receiving biological wastes.

As shown in FIGS. 1 and 2, the microfluidic cartridge 1 comprises three main elements, i.e.: the cartridge plate 10, the cartridge body 20 and the cartridge cover 30.

The microfluidic cartridge 1 also comprises a sample tube 40 containing a sample §., at least an amplification-mix tube 50 and a syringe 60.

These different elements of the microfluidic cartridge 1 will be detailed hereinafter.

The cartridge plate 10 of the microfluidic cartridge 1 first comprises a substrate 100 such as the one shown in detail in FIG. 7.

This substrate 100 has substantially the shape of a thin blade and has a first face 101 and a second face 102. The second face 102 is the face that is turned toward the cartridge body 20 when the cartridge is assembled (see FIGS. 1 and 2).

The cartridge plate 10 may advantageously be made by injection molding of a thermoplastic polymer material such as the cyclic olefin copolymers (COC) or the cyclic olefin polymers (COP). The cartridge plate 10 is here preferably made of polypropylene (PP). The COC and COP are amorphous and transparent materials based on cyclic olefins, whose biocompatibility is excellent. These materials allow the making of a sealed connection with a membrane and/or adhesive patches. They may in particular by chosen in the group comprising polycarbonate, polyacrylamide, polyethylene, polymethyl-methacrylate (PMMA), polydimetyl-siloxane (PDMS), polyvinyl chloride (PVC).

Preferably, the dimensions of the substrate 100 of the cartridge plate 10 are approximately, lengthwise and widthwise, comprised between 50 and 150 mm long, preferentially between 85 and 125 mm and 25 and 75 mm wide, preferentially between 40 and 60 mm. The thickness of the substrate 100 is preferentially comprised between approximately 1 and 5 mm, preferentially between 1 and 2 mm.

Generally, the microfluidic cartridge 1 includes a fluidic network of microchannels in which various fluids circulate and which each comprise at least one valve for controlling the circulation of such fluids in the corresponding microchannels.

It will now be described, for the particular embodiment of the microfluidic cartridge 1 shown in FIGS. 1 and 2, where and how are formed these microchannels and the associated valves with reference to FIGS. 7 to 11 showing various views of the cartridge plate 10 and the substrate 100 thereof.

Therefore, as shown in particular in FIGS. 7 and 8, the cartridge plate 10 first includes a plurality of through holes, which are herein as a matter of reference in a total of thirty-four and which are referenced:

H1 to H14,
H0c to H5c, and H9c, H10c, and
H7a, H7b, H11a, H12a, H15a to H15d, H16a to H16d.

Figure 9:
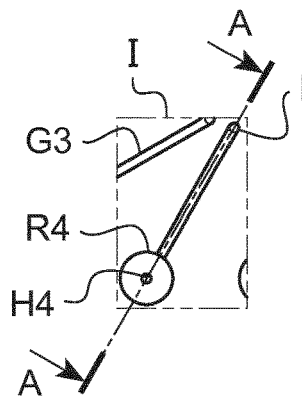
FIG. 9 is a detailed view of the area referenced I in FIG. 8.
Figure 9A:
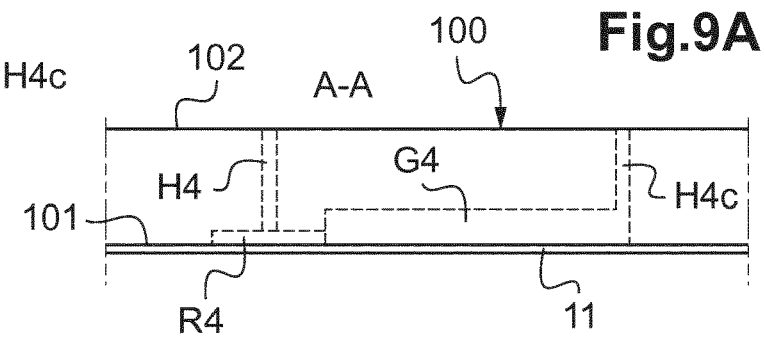
FIG. 9A is a sectional view of FIG. 9 according to the section plane A-A.
Figure 10:
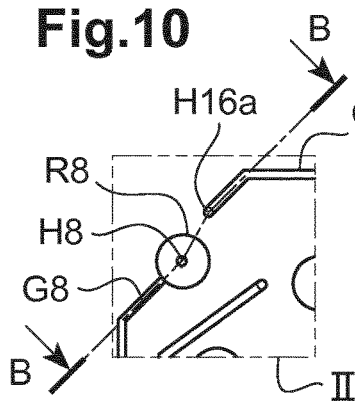
FIG. 10 is a detailed view of the area referenced I in FIG. 8.
Figure 10A:
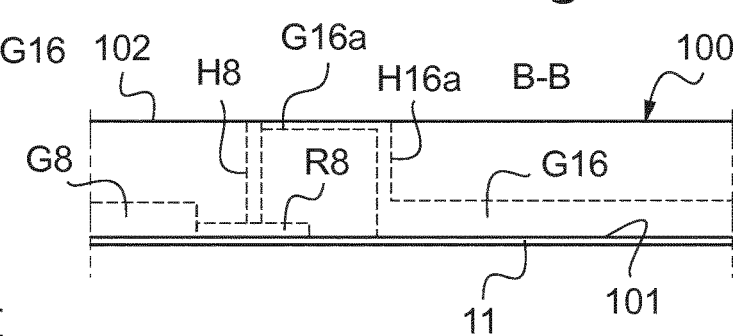
FIG. 10A is a sectional view of FIG. 10 according to the section line B-B.

All these through holes extend through the substrate 100, between the first face 101 and the second face 102, and preferably perpendicularly to these two faces 101, 102 (see for example FIGS. 9A and 10A, respectively, for the through holes H4, H4C, and the through holes H8, H16a).

These through holes, opening on each of the first and second faces 101, 102, fluidically connect elements from either face to each other. It is meant by this that a fluid can circulate in these through holes, in one direction as in the other.

For a proper understanding, the distinction will be made, in the following description, between three different types of through holes (see FIGS. 7 to 10A):
a. the through holes with recess: these are the through holes referenced H1 to H14 (see FIGS. 8, 9 and 9A), flow through them is actuated by valves
b. the central through holes: these are the through holes referenced H0c to H5c, H9c and H10c, and
c. the simple through holes corresponding to the remaining through holes and referenced H7a, H7b, H11a, H12a, H15a to H15d, H16a to H16d.

The through holes with recess, referenced H1 to H14 in FIGS. 7 and 8, each have, at their end turned toward the first face 101 of the substrate 100, a recess, referenced R1 to R14, respectively, in FIGS. 7 and 8, cylindrical in shape, made at the surface of the first face 101 of the substrate 100. This is, for example, illustrated in FIGS. 9A and 10A, which are partial sectional views of the substrate 100, where the through holes H4 (FIG. 9A) and H8 (FIG. 10A) are shown with their respective recess R4 and R8.

The recesses R1 to R14 have:
a. a diameter comprised between 1 mm and 10 mm, preferentially between 2 mm and 8 mm, preferably of about 4 mm, and
b. a depth comprised between 0.02 mm and 0.4 mm, preferentially between 0.05 mm and 0.15 mm, preferably of about 0.1 mm.

The central through holes, referenced H0c, H1c, H2c, H3c, H4c, H5c, H9c and H10c (see for example FIG. 8), which are close to each other are arranged herein in a circle. The interest of such an arrangement will be seen hereinafter.

Besides, the cartridge plate 10 includes a first plurality of sixteen grooves, referenced G1 to G16 in FIGS. 8 to 10A. These first grooves G1 to G16 are made in the vicinity of the first face 101 of the substrate 100, in such a manner to flush with this first face 101. This may be observed, for example, in FIGS. 9A and 10A, in which the grooves G4 (FIG. 9A) and G8, G16 are shown.

Advantageously, these grooves G1 to G16 are parallel to the first face 101 of the substrate 100, having a depth generally comprised between 0.01 mm and 0.5 mm, preferentially between 0.2 mm and 0.4 mm, preferably of about 0.3 mm.

The width of these grooves G1 to G16 is herein equal to about 0.5 mm.

In the particular embodiment of the microfluidic cartridge 1 shown in FIG. 1, it is observed that these first grooves G1 to G16 extend (see FIG. 8):
a. either between a central through hole H0c, H1c, H2c, H3c, H4c, H5c, H9c, H10c and a recess R1 to R10: this is the case of the grooves G1 to G10 (see for example FIG. 9A for the groove G4 between the central hole H4c and the through hole G4 with its recess R4);
b. or between the central through hole H0c and a simple through hole H11a, H12a: this is the case of the grooves G11 and G12;
c. or between two simple through holes: this is the case of the grooves G15 and G16 that extend between the through holes H15a and H15c, and between the through holes H16a and H16c, respectively. Regarding these particular grooves G15, G16, it is also observed that they respectively comprise on their way a simple through hole H15b, H16b.

The grooves G6, G7, G8, G11 and G12 share a common part that connects each of these grooves G6, G7, G8, G11, and G12 to the central hole H0c, and form this way a branched structure.

Figure 11:
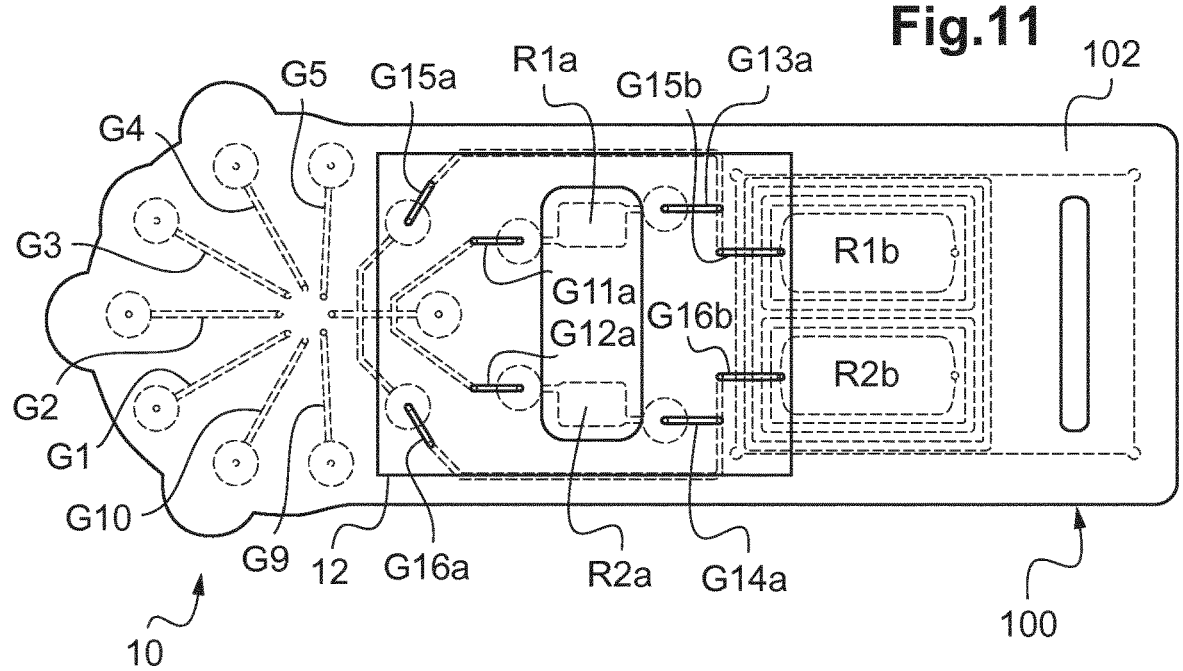
FIG. 11 is a top view of the cartridge plate of FIG. 7.

As shown in FIGS. 7 and 11, the cartridge plate 10 finally comprises a second plurality of eight grooves G11a, G12a, G13a, G14a, G15a, G15b, G16a, G16b. These second grooves G11a, G12a, G13a, G14a, G15a, G15b, G16a, G16b, are made in the vicinity of the second face 102 of the substrate 100, in such a manner to flush with this second face 102. This may be observed, for example, in FIG. 10A, in which the groove G16a is shown.

As for the first grooves G1 to G16, these second grooves G11a, G12a, G13a, G14a, G15a, G15b, G16a, G16b, are advantageously parallel to the second face 102 of the substrate 100. They have the same dimensional characteristics as the first grooves G1 to G16.

Generally, and as it can be understood by observing FIG. 8 (bottom view of the substrate 100) and FIG. 11 (top view of the substrate), the second grooves G11a, G12a, G13a, G14a, G15a, G15b, G16a, G16b, formed on the second face 102 of the substrate 100 extend:
a. either between a through hole H6, H8, H11, H12, H13, H14, with recess, and a simple through hole H15a, H16a, H11a, H12a, H15b, H16b, respectively: this is the case, for example, of the second grooves G11a, G12a, G13a, G14a, G15a and G16a (see for example FIG. 10A);

b. or between two simple through holes H15c, H15d, H16c, H16d: this is the case for example of the groove G15b (between the simple through holes H15c, H15d) and of the groove G16b (between the simple through holes H16c, H16d).

The through holes, recesses and grooves made in the above-mentioned substrate 100 are intended to form, on the one hand, the fluidic network of microchannels, and on the other hand, the fluid control valves in these microchannels.

For that purpose, it is understood that it is necessary to close the through holes, recesses and grooves that are, as just described, open to the first surface 101 or the second surface 102 of the substrate.

Therefore, the cartridge plate 10 first comprises a first film 11 (see FIG. 2) that, when the microfluidic cartridge 1 is assembled (see FIG. 1), is located on the first face 101 of the substrate 100 of the cartridge plate 10.

Moreover, the form and dimensions of this first film 11 are adjusted so as (see FIG. 8):

a. to follow the outer profile 103 of the substrate 100, and
b. to extend over a large half of the substrate 100 so as to cover the whole of the first grooves G1 to G16, the recesses R1 to R14, and the central through holes H0c to H5c, H9c, H10c, and the simple through holes H11a, H12a, H15a to H15c, and H16a to H16c.

The first film 11 is preferentially made in a material similar to the rigid substrate 100 of the cartridge plate 10. Generally, the first film 11 is here made of polypropylene (PP).

Preferentially, the first film 11 is a thermoplastic film of about 0.1 mm thick, bonded or welded to the surface of the first face 101 of the substrate, by thermo-welding, e.g. by laser-welding, bonding, adhering or chemical linking methods. This first film 11 closes the first face 101 and provides the thickness of the microfluidic circuit.

Thus positioned and fixed on the first face 101 substrate 100, the first film 11 closes and tightly seals the first grooves G1 to G16, the recesses R1 to R14, and the central through holes H0c, H1c à H5c, H9c, H10c, and the simple through holes H11a, H12a, H15a to H15c, and H16a to H16c.

In other words, the first film 11 cooperates with the first grooves, the through holes and the recesses to form a plurality of microfluidics channels, or microchannels, and valves.

Figure 12:
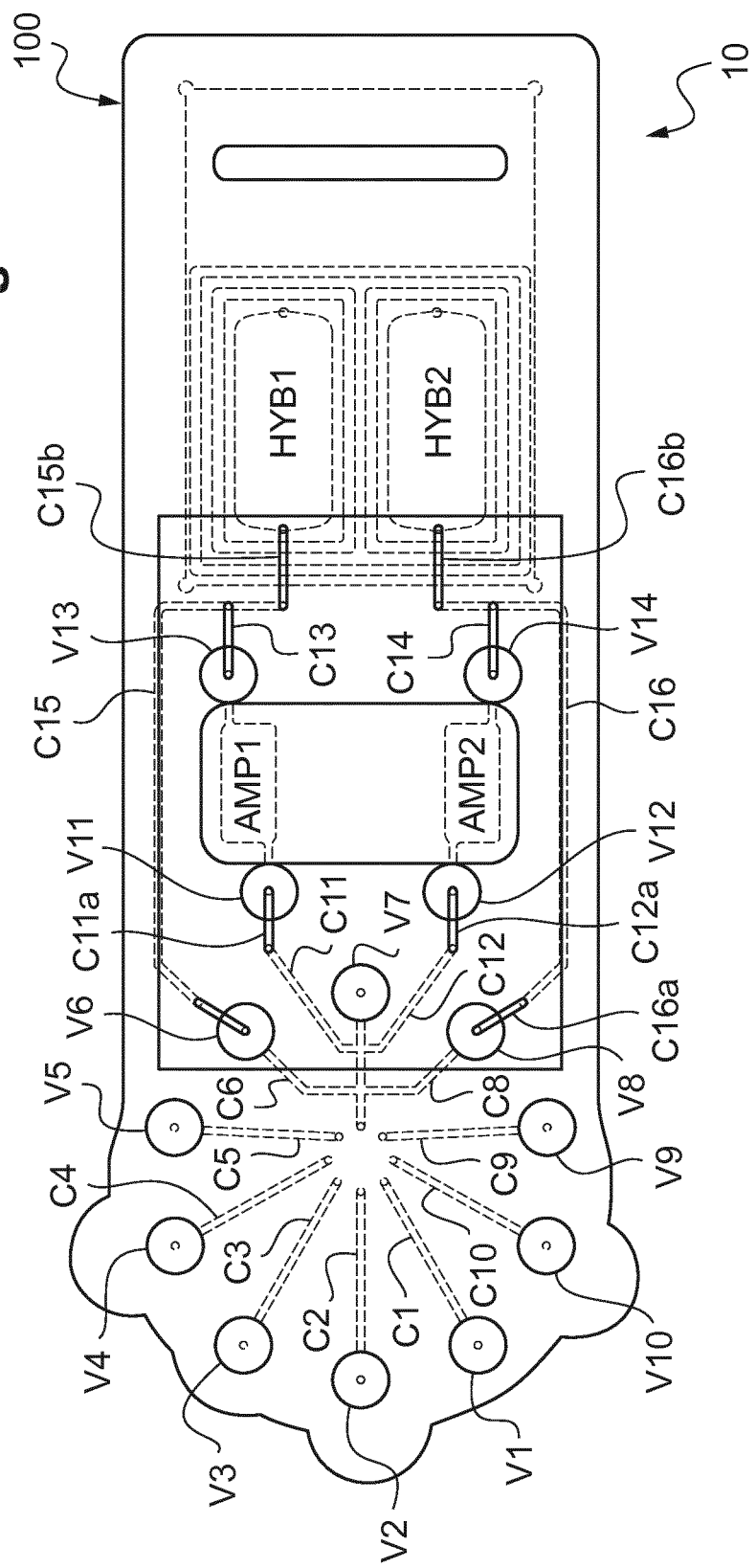
FIG. 12 is a schematic view of the mounting of the microfluidic cartridge of FIG. 1 in a docking station in a preferred embodiment (mechanical part only)

As shown in FIG. 12, microchannels C1 to C12, C15, C16, are thus formed by the closing of the first grooves G1 to G12, G15, G16, flush with the first face 101 of the substrate 100 by means of the first film 11 deposited on this first face 101.

In the same manner, the valves V1 to V14 are formed by the deformable first film 11 placed opposite a valve seat formed by the recessed R1 to R14 formed at the surface of the first face 101 of the substrate 100.

In a preferred manner, the surface of the deformable first film 11, placed opposite the recesses R1 to R14 is, at rest, approximately planar and parallel to the first face 101 of the substrate, and capable of being deformed by an external actuator (see infra). The deformation of the first film 11 at the level of the recesses R1 to R14 under the action of this external actuator allows opening or closing the valves V1 to V14.

More precisely, the deflection of the first film 11 opposite each valve seat, i.e. each recess R1 to R14, allows the obturation of the corresponding through holes H1 to H14, whose diameter is far lower than that of each recess R1 to R14. This allows the making of a maximum obturation of the cartridge plate 10 while using a first film 11 having certain rigidity.

The cartridge plate 10 also comprises a second film 12 (see FIG. 2), or a plate, that, when the microfluidic cartridge 1 is assembled (see FIG. 1), is located on the second face 102 of the substrate 100 of the cartridge plate 10.

The second film 12 is herein made of a material similar to the rigid substrate 100 of the cartridge plate 10 and its thickness, of about 0.1 mm.

Alternatively, a plate may be used. This plate can have dimensions comprised between 0.05 mm and 2 mm.

The second film 12 is bonded to the second face 102 of the substrate 100 by bonding. As a variant, the second film may be fixed on the second face by thermo-welding, adhering or chemical linking methods.

This second film 12 closes the second face 102 and allows the tightness of the microfluidic circuit.

More precisely, the second plurality of grooves G11a, G12a, G13a, G14a, G15a, G15b, G16a, G16b, is closed and sealed by the second film 12.

As for the first film 11, and as shown in FIG. 12, microchannels C11a, C12a, C13, C14, C15a, C15b, C16a, C16b, are thus formed by the closing of the second grooves G11a, G12a, G13a, G14a, G15a, G15b, G16a, G16b, flush with the second face 102 of the substrate 100 by means of the second film 12 deposited on this second face 102.

The second film 12 has a rectangular opening 12A (see FIG. 2) so as to allow the passage thereof through the cartridge body 20 during the assembly of the microfluidic cartridge 1.

The first film 11 and the second film 12, thus applied on the substrate 100 of the cartridge plate 10, form with it the fluidic network of microchannels C1 to C15, C11a to C16a, C15b, C16b (see FIG. 12).

It will be seen hereinafter how the microchannels and the valves formed in the cartridge plate 10 are used to transport and transfer the fluids required for the analysis of the sample.

As shown in FIGS. 8 and 11, the cartridge plate 10 also includes at least two recessed cavities R1a, R2a separated from each other and formed in the substrate 100. These two recessed cavities R1a, R2a are made in the first face 101 and extend from the latter toward the inside of the substrate 100 (see FIG. 8A).

The two recessed cavities R1a, R2a are tightly closed by the first film 11 deposited on the first face 101 of the substrate 100, in such a manner to form two reaction chambers for nucleic acid amplification, called hereinafter amplification chambers and referenced AMP1 and AMP2 (see FIG. 12).

The circulation of the fluids toward or out of these two amplification chambers AMP1, AMP2 is controlled by the valves V11, V13 and by the valves V12, V14, respectively.

The valves that control the circulation of the fluids between the amplification chambers (typically V13 and V14) are actuated by linear actuators that are independent of the cam-driven actuator. Preferentially the valves that control the circulation of the fluids toward the amplification chambers (typically V11 and V12) are actuated by linear actuators that are independent of the cam-driven actuator.

In the same way, as shown in FIGS. 8 and 11, the cartridge plate 10 includes two other recessed cavities R1b, R2b and formed in the substrate 100.

Figure 8B:
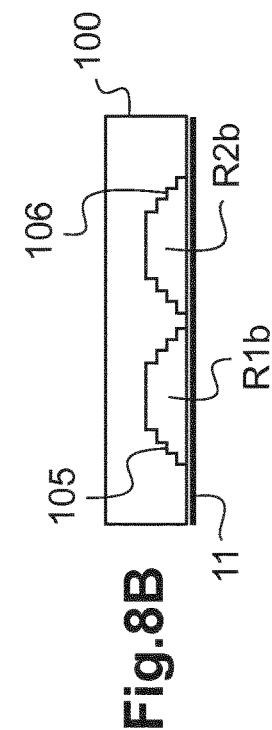
FIG. 8B is a sectional view of FIG. 8 according to the section plane B-B.
Figure 8A:
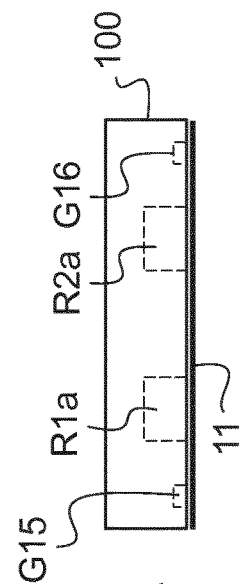
FIG. 8A is a sectional view of FIG. 8 according to the section plane A-A.

These two recessed cavities R1b, R2b, substantially parallelepiped in shape, are made in the first face 101 and extend from the latter toward the inside of the substrate 100. As shown in FIG. 8B, the two recessed cavities R1*b*, R2*b* have indented inclined flanks 105, 106, respectively.

These two recessed cavities R1*b*, R2*b* are tightly closed by a biochip 110 (see FIG. 2) bonded on the first face 101 of the substrate 100, so as to form two reaction chambers for nucleic acid analysis, called hereinafter hybridization chambers and referenced HYB1 and HYB2 (see FIG. 12).

The circulation of the fluids toward or out of these two analysis chambers HYB1, HYB2, is made through the through holes H7*a*, H15*d* (for the hybridization chamber HYB1) and through the through holes H7*b*, H16*d* (for the hybridization chamber HYB2), respectively.

In one embodiment, the cartridge may include, upstream from each amplification chamber, a metering chamber, located between the central HUB and each amplification chamber. For example said metering chambers are connected to the said amplification chambers through valves V11 and V12 (see FIG. 12) or VV8 and VV14 (see FIG. 16).

Typically said metering chambers are also connected to the central HUB, for example via microchannels C11 and C12. Alternatively, or additionally, said metering chambers can also be directly connected, through a microchannel, to a valve of a hub-connected microchannel. Said metering chambers are useful for calibrating the proper fluid level to be injected to the amplification chambers.

The hybridizations chambers comprise an affinity biosensor for detecting the presence of specific target molecules in the sample. The affinity biosensors interact with the target molecule by ligation. The cartridge according to the present invention is intended to allow the detection in parallel of the presence of several molecular hybridization markers within a biological sample. The capture of the amplification products, or amplicons, among a multiplicity of candidates on a surface is a technique that is well known of the one skilled in the art, to perform a multiplexed detection. The favorite mode of detection is the biochip. The biochip systems are presently widely used for the detection and the measurement of specific substances in complex samples. With such a biochip, the identity and quantity of a target DNA in a sample are measured by measuring the level of association of the target sequence with probes specifically provided for said sequence. In the DNA biochip technologies, a set of probe nucleic acids, each having a defined sequence, is immobilized on a solid support or substrate in such a way that each probe occupies a predetermined position.

According to the embodiment as exemplified in the present application, the biochip 110 essentially includes a solid substrate 111, approximately planar, for example a glass, silicon or plastic plate, on the surface of which are immobilized probe molecules, whose sequence is specific for target nucleic acids. As a matter of example the size of a biochip well suited for the cartridge of the invention is approximately of 24 mm×24 mm×0.1 mm.

The cartridge body 20 of the microfluidic cartridge 1 will now be described with reference to FIGS. 1, 2 and 6.

Preferably, the cartridge body 20 is made separately from the cartridge plate 10. In this case, the cartridge body 20 is made in three dimensions, advantageously by injection molding of a thermoplastic polymer material such as polypropylene (PP).

In a variant, the cartridge body may be made out of cyclic olefin copolymers (COC) or cyclic olefin polymers (COP), in particular chosen in the group comprising polycarbonate, polyacrylamide, polyethylene, polymethyl-methacrylate (PMMA), polydimetyl-siloxane (PDMS), polyvinyl chloride (PVC).

In some embodiments, the cartridge body is made in three dimensions for example by stereolithography or by sintering.

According to another advantageous variant, the cartridge body and the cartridge plate may be fabricated together so as to form a single piece. In this case, said piece is made for example by injection molding using the same kind of materials used for the cartridge plate 10 and for the cartridge body 20.

When the microfluidic cartridge 1 is assembled (see FIG. 1), this cartridge body 20 is in contact with the cartridge plate 10 on the second face 102 of the substrate 100, at the level of the first edge 22 of the cartridge body 20.

As shown in FIG. 2, the cartridge body 20 includes a lateral wall 21 extending perpendicular to the substrate 100, from the second face 102 of this substrate 100 to a second edge 23 of the cartridge body 20.

The cartridge body 20 also includes a plurality of internal walls W0, W1, W2, W3, W4, W5, W6, W7, W8, W9, W10, which define a plurality of functional volumes CT, T1, T2, T3, T4, T5, AMP, DET, T9, T10, respectively (see FIG. 2).

These different functional volumes CT, T1, T2, T3, T4, T5, AMP, DET, T9, T10, of the cartridge body 20 are containers intended to receive, during the use of the microfluidic cartridge 1 for the analysis of the sample S, the sample S, which is treated or not, different reagent products, a purification column, as well as fluids or solids intended to the preparation, the amplification and the analysis of the sample S.

The functions of these different functional volumes will be described hereinafter.

Besides, as shown in FIG. 2, it is observed that the lateral wall 21 and the six internal walls W0, W5, W6, W7, W8, W9, also define the functional volume WST that, as will be seen hereinafter, is a volume for the wastes coming from the sample S and from the different reagent products.

When the microfluidic cartridge 1 is assembled (see FIG. 1), the cartridge body 20 being fixed to the cartridge plate 10 at the level of the second face 102, each functional volume T1, T2, T3, T4, T5, T9, T10, CT, WST, AMP, DET, is closed at the level of the first edge 22 of the cartridge body 20 by the first face 102 of the substrate 100, such that:

a. the functional volumes T1, T2, T3, T4, T5, T9, T10 comprise the through holes H1, H2, H3, H4, H5, H9, H10, respectively;

b. the functional volume CT surrounds and comprises the whole of the central through holes H0*c*, H1*c*, H2*c*, H3*c*, H4*c*, H5*c*, H9*c*, H9*c*, H10*c*;

c. the functional volumes AMP et DET surround the two amplification chambers AMP1, AMP2, and the two detection chambers HYB1, HYB2, respectively;

d. the functional volume WST is in communication with the through holes H7, H7*a*, and H7*b*.

Thus, it is understood (see in particular FIG. 12) that the functional volumes T1, T2, T3, T4, T5, T9, T10, are, each independently, in fluidic communication with the functional volume CT via the microchannels C1, C2, C3, C4, C5, C9, C10 controlled by the valves V1, V2, V3, V4, V5, V9, V10, and fluids can circulate, in one direction as in the other, between these different functional volumes.

For that purpose, the functional volume CT, also called central tube, forms a hub body into which, or out of which, a syringe 60 (see FIGS. 1 and 2) can slide.

More precisely, as shown in FIG. 4, the syringe 60 includes a plunger 62 and a plunger seal 61, in which the plunger 62 is fixed. For example, the plunger 62 may be attached to the plunger seal 61 by inserting in force the plunger 62 into the plunger seal 61 comprising deformable attaching means.

The plunger 62 also comprises, on the opposite side with respect to the plunger seal 61, a flat 63 making it possible to push or pull on this plunger 62 to make the syringe 60 slide in the hub body CT.

The plunger seal 61 of the syringe 60 comprises two O-rings 61A, 61B and has an outer diameter adjusted in such a manner that, once engaged in the central tube CT, it can tightly slide in the central tube CT.

That way, the syringe 60 can pump or inject fluids in the different functional volumes T1, T2, T3, T4, T5, T9, T10, that are connected to the central tube CT through microchannels C1, C2, C3, C4, C5, C9, C10.

In a preferred embodiment, only the plunger seal 61 is part of the cartridge body 20 of the microfluidic cartridge 1. In this preferred embodiment, the plunger 62 of the syringe 60 is part of the docking station 1000. Therefore, the number of moving parts in the microfluidic cartridge 1 is reduced, like its cost of fabrication.

It will then be considered that the hub body CT and the syringe 60 are part of a central distribution hub of fluids, hereafter called central hub and referenced with the reference sign CH.

As can also been understood from FIG. 12, this central hub CH is also capable of pumping or injecting fluids:
a. from or to the waste container WST via the microchannel C7, and thanks to the valve V7;
b. from or to the amplification chambers AMP1, AMP2, via the microchannels C11, C11a, C12, C12a and thanks to the valves V11, V12;
c. from or to the detection chambers HYB1, HYB2, via the microchannels C6, C8, C15a, C16a, C15, C16, C15b, C16b, thanks to the valves V6, V8.

In one embodiment of the microfluidic cartridge, the valves associated with the waste container or with the detection chambers are not located on hub-connected microchannels, and therefore are actuated by linear actuators that are independent of the cam-driven actuator.

As shown in Figures and 2, the cartridge cover 30 of the microfluidic cartridge 1 comes and inserts into the cartridge body 20, resting on its second edge 23 so as to close the different functional volumes T2, T4, T5, T9, T10, WST, AMP, DET.

As the cartridge plate 10 and the cartridge body 20, the cartridge cover 30 is made advantageously by injection molding of a thermoplastic polymer material such as polypropylene (PP).

In a variant, the cartridge cover may be made by injection molding of a thermoplastic polymer material such as, for example, the cyclic olefin copolymers (COC) or the cyclic olefin polymers (COP), in particular chosen in the group comprising polycarbonate, polyacrylamide, polyethylene, polymethyl-methacrylate (PMMA), polydimetyl-siloxane (PDMS), polyvinyl chloride (PVC).

The cartridge cover 30 comprises venting holes 32 at the level of each functional volume T2, T4, T5, T9, T10, so as to permit the suction and the injection of fluids in these volumes of the central hub CH.

In an assembled configuration (FIG. 1), before the use of the microfluidic cartridge 1 for the analysis of the sample S, the cartridge cover 30 comprises a protection film 31 tightly covering the whole of the venting holes 32, so as to protect the content of the functional volumes T2, T4, T5, T9, T10, during transportation or storage of the microfluidic cartridge 1. This protection film 31 may be for example made of a plastic or metallic (e.g. aluminum) thin sheet.

In one embodiment, the microfluidic cartridge may further comprise a semi-permeable membrane between the cartridge body and the cartridge cover. This semi-permeable membrane comprises, on one side, a hydrophobic layer and, on the other side, an adhesive layer in order to seal the membrane to the second edge of the cartridge body.

The semi-permeable membrane acts as a GORETEX™ fabric, and is adapted to let air pass through it while preventing liquids to leak out of the functional volumes. Therefore, this semi-permeable membrane allows the venting of the various functional volumes of the microfluidic cartridge.

As shown in FIGS. 1 and 2, the microfluidic cartridge 1 also includes herein two tubes 40, 50, which are assembled in the microfluidic cartridge 1 during the use thereof, by plunging into the tube T1 and the tube T3, respectively, of the cartridge body 20.

The first tube 40, that contains the sample S, is a sample tube that comprises (see FIG. 3) a body 42 of cylindrical shape, a cap 41 closing the body 42 on one side of the tube, and a terminal opening 43 located on the other side of the tube. The cap 41 may contain a semi permeable membrane allowing air flow while retaining liquids.

According to the embodiment as exemplified in the present application, the terminal opening 43 is here closed by a plastic bead 44 according to a technology similar to that of the disposable ink cartridges.

In particular, the container T1 intended to receive the sample tube 40 comprises a suction head designed to push the plastic bead 44 so as to eject the plastic bead 44 from its blocking position, where it prevents the flowing of the content of the sample tube 40.

In a variant, the sample may be injected directly into the container, either by using a tube without suction head or by pipetting the sample with a micropipette or syringe into the dedicated container.

Besides, the sample tube 40 also comprises a filter 45 placed inside the body 42 of the tube 40, so as to limit the quantity of large particles, coming from the sample S or from by-products of the sample S, entering into the microfluidic network.

The second tube 50 is a tube that comprises a mixture for the amplification reaction, referred to as amplification-mix tube, which is has a shape similar to that of the first tube 40 with a body 51, a cover 52, and a terminal part 53 also comprising a closing bead (not shown).

The above-described microfluidic cartridge 1 is intended to be inserted in a docking station 1000, a partial sectional view of which is shown in FIG. 13.

In the embodiment shown in FIG. 13, the docking station 1000 includes a rotational-motion cam-driven actuator 1100.

More precisely, the cam-driven actuator 1100 includes a cam 1120 (see FIG. 15), which is herein an annular cylindrical part 1121 around an axis of revolution A1, which has a first surface 1121A and a second surface 1121B, substantially planar and parallel to each other, and a central opening 1123.

Advantageously, the cam 1120 comprises on its first surface 1121 a rectilinear cam recess 1124 extending along a radius of the cylindrical part 1121. The profile of this cam recess 1124, considered along a perimeter of the annular part 1121, is herein curved and has, on the bottom of the cam recess 1124, a radius of curvature Rc.

The cam-driven actuator 1100 also comprises a planar guiding plate 1110 (see FIGS. 13 and 14), herein perforated with ten cylindrical holes 1111 arranged circularly and passing perpendicularly through the guiding plate 1110. These guiding holes 1111 are intended to guide ten actuating balls 1102 of the cam-driven actuator 1100 (see FIG. 13, where only one actuating ball 1102 is shown), such actuating balls having a ball diameter adjusted so that they can slide through said guiding holes 1111 without rubbing excessively on the walls of these latter.

As shown in FIG. 13, the guiding plate 1110 of the rotational-motion cam-driven actuator 1100 is located above the cam 1120 so that the actuating balls 1102 rest on the first surface 1121A of the cam 1120.

Besides, the radius of the cylindrical holes 1111, and thus the diameter of the actuating balls, is adjusted with respect to the thickness of the guiding plate 1110 so that:
   a. in the case where an actuating ball 1102 rests on a planar part of the first surface 1121A of the cam 1120 (the case of FIG. 13), the actuating ball 1102, maintained in place by its corresponding cylindrical hole 1111, projects upward from the guiding plate 1110;
   b. in the case where an actuating ball 1102 rests on the cam recess 1124 of the annular part 1121 of the cam 1120, the actuating ball 1102, guided by its corresponding cylindrical hole 1111, projects downward from the guiding plate 1110.

Therefore, upon a rotational motion of the cam 1120 around the axis of revolution A1, the actuating ball 1102 performs a translation motion parallel to said axis of revolution A1, the actuating ball 1102 being guided thanks to the corresponding cylindrical hole 1111 between an engaged position where the actuating ball 1102 projects from the cylindrical hole 1111, while moving far from the cam 1120, and a disengaged position where the actuating ball 1120 move closer to the cam 1120.

In the preferred embodiment shown in FIG. 15, where the cam 1120 comprises only one cam recess 1124, at most one actuating ball 1102 can be in a disengaged position while the other actuating balls 1102 are in an engaged position.

As shown in FIG. 13, the cam actuator 1100 comprises a series of ten plungers 1101 each located above an actuating ball 1102 and another guiding plate 1130, similar to the first guiding plate 1110, which is also perforated so as to guide the plungers 1101 in their translation motion.

In the cam-driven actuator 1100, the cylindrical holes 1111, the actuating balls 1102 and the plungers 1101 are arranged circularly.

In the microfluidic cartridge 1 according to the invention, the ten valves V1 to V10 are arranged so as to be mechanically actuated together by the external cam-driven actuator 1100.

More precisely, the valve V1 to V10 of the microchannels C1 to C10 connected to the central hub CH are arranged circularly so that there is a plunger 1101 opposite each of the valves V1 to V10.

So arranged, it is understood that:
   a. when an actuating ball 1102 is in an engaged position (the case of FIG. 13), it places the corresponding plunger 1101 also in an engaged position where it exerts a pressure on the first film 11 of the cartridge plate 10, opposite the valve seat R1 of the valve V1, so as to deform the first film 11 and to seal the through hole H1, thus closing the valve V1, and
   b. on the contrary, when an actuating ball 1102 is in a disengaged position, the plunger 1101 also goes to a disengaged position where it does not exert any more pressure to the first film 11 of the cartridge plate 10, so that the first film 11 is at rest opposite the valve seat R1 of the valve V1, so that the valve V1 is then open.

Therefore, as seen above, it is understood that the cam-driven actuator 1100 allows the opening of at most one valve V1 to V10 at the same time when the microfluidic cartridge 1 is inserted in the docking station 1000 and when the microfluidic station 1 is actuated by the cam-driven actuator 1100.

Although it is not shown, the docking station 1000 in the embodiment shown in FIG. 13 also includes sliding means to make the syringe 60 of the central hub CH slide into and out of the hub body CT.

These sliding means may comprise, for example, the plunger 62 of the syringe 60 and a fork-shape lever that catches the plunger 62 of the syringe 60, below the flat 63, so as to lower down or lift up the plunger 62.

Besides, as already known, the docking station 1000 also comprises:
   a. optical excitation means for exciting the biochip 110 in contact with the two hybridization chambers HYB1, HYB2, and
   b. optical detection means for detecting an optical signal emitted from the hybridization chambers HYB1, HYB2 and that is representative of the at least one nucleic acid searched in the sample S analyzed by the microfluidic cartridge 1.

In this embodiment wherein the detection biochip 110 is used, the detection and quantification of the interaction between the target molecules and the probe is made to a device for optical detection: light radiation of a first wavelength excites chromophores linked to the target molecules. The light emitted by the chromophore at a second wavelength in response to their excitation light is then collected by a collection device.

It is also particularly advantageous that the present microfluidic cartridge 1, and thus the reading of the biochip 110, be suitable for a system for collecting the light emitted by the chromophore in response to light excitation type contact imaging.

It can be considered that the microfluidic cartridge 1 is intended to be placed in an apparatus for reading optical contact imaging. Such contact imaging devices have been notably described in WO 2004042376, WO 2004068124, WO 2007045755, WO 2010007233 and WO 2012089987.

Advantageously, the substrate 100 is transparent.

In the case of detection of target nucleic acids by means of a biochip 110 fluorescence, it may be advantageous that the substrate of the biochip 110 may comprise fluorescent substances immobilized on its surface which absorbs light at a first excitation wavelength and emit light at a second wavelength transmission, comprises means for increasing the efficiency of the amount of light emission based on the amount of excitation light.

A method intended to be implemented by an operator in order to analyze the sample S contained in the sample tube 40, said tube being inserted in the functional volume T1 of the microfluidic cartridge 1 (see FIG. 2), will now be described.

The sequence of operations performed by the diagnostics machine may comprise the following steps:
   a. DNA extraction & purification from the lysed sample
   b. DNA amplification using any amplification method including but not limited to Polymerase Chain Reaction (PCR), Reverse transcriptase PCR and isothermal amplification;

c. Hybridization on a microarray using highly-specific probes (such as the Hairloop™ probes) or standard linear probes to discriminate markers up to SNP discrimination level.

d. Detection of hybridization by fluorescent labeling using a fluorescence integrated reader preferentially allowing contact-imaging devices integrated to the docking station such as described in WO 2004042376, WO 2004068124, WO 2007045755, WO2010007233 and WO 2012089987.

In one embodiment, a pre-lysis step is performed prior injection of the sample in the cartridge.

Lysis buffer and/or reagents can be added to the sample prior injection in the cartridge and/or stored in one functional volume of the cartridge, as lyophilized pellet.

The sample may be a solution or in suspension, in particular the sample may be a bodily fluid, such as feces, whole blood, plasma, serum, urine, sputum, saliva, seminal fluid, mucus and cerebrospinal fluid. The sample may also be a solid made soluble or suspended in a liquid.

By nucleic acid it is intended according to the present invention, any synthetic or naturally occurring nucleic acid in any configuration (single-stranded or double-stranded DNA).

It is noted that in some embodiments of the invention, the target nucleic acid may be in the form of RNA in the sample, typically when viral nucleic acid are searched in the sample to analyze. In such embodiment the nucleic acid may be subjected to RT PCR.

The main steps of this analysis method are performed in the functional volumes of the microfluidic cartridge 1 which comprises a plurality of functional areas comprising at least:
a. a sample preparation area comprising the different functional volumes designed to extract a specific nucleic acid from the sample S to analyze;
b. a nucleic acid amplification area comprising the functional volumes adapted to perform the amplification of the nucleic acid contained in the sample S. According to various embodiments, the nucleic acid amplification area comprises one or more amplification chambers;
c. a nucleic acid analysis area, typically comprising the functional volume T9 and T10. According to various embodiments, the nucleic acid amplification area comprises one or more detection chamber; and
d. a waste area comprising the functional volume WST designed for the waste.

In the preferred embodiment described above, the different functional areas are such that:
a. the sample preparation area comprises the sample tube 40, the amplification-mix tube 50, and the three functional volumes T2, T4, T5 comprising respectively a purification column, a first DNA wash buffer and a second DNA wash buffer;
b. the nucleic acid amplification area comprises the two amplification chambers AMP1, AMP2;
c. the nucleic acid detection area comprises the two functional volumes T9 and T10 comprising, respectively, a buffer for hybridization and a hybridization wash buffer.

Therefore, according to the embodiment of the microfluidic cartridge 1 described above in reference to FIGS. 1 and 2, the sample preparation area and the waste area are directly fluidly connected to the central hub CH of fluid distribution by one or more hub-connected microchannels and one or more cam-driven actuated valves. The nucleic acid detection area may optionally be directly fluidly connected to the central hub CH by one or more hub-connected microchannels (C15 and C16).

Still in the embodiment of the microfluidic cartridge 1 described in reference to FIGS. 1 and 2, the amplification area is not directly connected to the central hub CH and fluidic connection toward this area and notably to each amplification chamber is controlled by at least one valve actuated by a linear actuator.

As explained above, the central hub CH by means of the syringe 60 engaged in the central tub CT is able to transfer fluids from a first functional area to a second functional area of the plurality of functional areas by passing through it.

In the way the different functional areas are arranged in the microfluidic cartridge 1, said second functional area can be either identical or different from said first functional area.

Moreover, one will understand with the following description of the analysis method how the plurality of functional areas cooperates with each other in order to analyze the sample S.

Step a)

In a first step (step a), the operator provides the biological sample S into at least one functional volume of the sample preparation area of a microfluidic cartridge 1, namely here in the sample tube 40 which is inserted into the microfluidic cartridge 1.

At start-up, the sample tube 40 may already contains a lysis buffer. Disruption of most cells may be done by chaotropic salts, detergents or alkaline denaturation. The lysis of the sample S is typically performed through a Lysis and Proteinase K Buffer already present in the sample tube 40 when injecting the sample S into this tube 40.

Once the microfluidic cartridge 1 is inserted in the docking station 1000, the sample S is incubated during a few minutes to completely break down cellular membranes by the chemical lysis. The Proteinase K buffer finishes the digestion of protein cellular components.

In another embodiment, lysis buffer and reagents (such as protein K buffer) may also be stored in a functional volume of the cartridge as lyophilized pellet.

In another embodiment, where the sample comprises hard-to-treat matrix or microorganisms, the following steps might be necessary before insertion of the sample preparation tube into the microfluidic cartridge:
a. lysis of the sample using for example bashing beads together with a specific cell disruption buffer;
b. vortex and heat during a few minutes, for example 5 minutes, at a temperature up to 70° C.;
c. addition of Binding Buffer and potentially of a reagent allowing amplification Inhibitor absorption, such as InhibitEX Matrix, to the sample preparation tube.

Step b)

The sample S is put into contact with a reagent typically present in the purification column T2.

For this, the cam-driven actuator 1100 is rotated by the docking station 1000 and put in a position so as to actuate consecutively the valve V1 and the valve V2 in the following way:
a. valve V1 open and valve V2 closed: the plunger 62 of the syringe 60 is slid out of the central tube CT by the fork-shape lever of the docking station 1000 in order to pump the lysed sample S from the sample tube 40 to the central tube CT;
b. valve V1 closed and valve V2 open: the plunger 62 of the syringe 60 is slid in the central tube CT by the fork-shape lever of the docking station 1000 in order to inject the lysed sample S from the central tube CT into the purification column T2.

The purification column T2 may contain a silica-like membrane for DNA binding.

According to various embodiments, the purification column may for example contain a gel, beads, or a paper filter for DNA binding and concentration. As a matter of illustration, agarose gel, silica beads and filter paper, such as cellulose, base purification may also be used according to the invention.

Once the binding is completed, the sample S is re-aspirated from the purification column (valve V2 open), and disposed to the waste area through the central hub CH with valve V7 open, while the DNA is retained by the purification column T2.

Step c)

In this step, the product resulting of step b) is recovered by washing it in order to remove inhibitors and purify the DNA.

In the embodiment as exemplified in the present application, the binding membrane of the purification column T2 is washed successively by one or more DNA wash buffers, typically two, as contained in the functional volumes T4, T5.

To this end, firstly, the valve V4 is open (all other valves being closed) by the cam-driven actuator 1100 and the first DNA wash buffer contained in the functional volume T4 is pumped out by the central hub CH and then the valve V2 is open (valve V4 being therefore automatically closed) and the central hub CH injects the first DNA wash buffer in the purification column T2.

Secondly, the same operation is repeated with the second DNA wash buffer contained in the functional volume T5 (valve V2 closed/valve V5 open and then valve V2 open/valve V5 closed).

Thirdly, the DNA bound to the binding membrane is eluted with an elution buffer. The amplification-mix solution contained in the amplification-mix tube T3 can be used as an elution buffer. For that, valve V2 is closed, valve V3 is opened thanks to the rotation of the cam-driven actuator 1100 of the docking station 1000, and the central hub CH sucks out the amplification-mix solution into the central tube CT; then valve V3 is closed, valve V2 is opened, and the syringe 60 is slid into the central tube CT so that the central hub CH injects the PCR-mix solution into the purification column 20.

At the end of step c), one obtains an isolated DNA sample.

Step d)

After elution, the isolated DNA sample amplification-mix is transferred into the two amplification chambers AMP1, AMP2 for amplification.

For that, the isolated DNA sample is pumped from the purification column T2 (valve V2 still open) to the central tube CT.

Then, all valves V1, V2, V3, V4, V5, V6, V7, V8, V9, V10 are closed by actuation of the cam-driven actuator 1100.

The valve V11 and V12 of the microfluidic cartridge 1, which are independently actuated by two standard linear actuators, are opened, allowing of the isolated DNA sample to go through the micro-channels C11, C11a, C12, C12a to the two amplification chambers AMP1, AMP2.

In some embodiments, the isolated DNA sample amplification-mix is transferred to a metering chamber prior to transfer to each amplification chamber (AMP1 and AMP2), in order to calibrate the proper volume to be injected in the said amplification chambers.

Step e)

During this step, after the valves V11, V12 of the nucleic acid amplification area have been closed, the isolated DNA sample is put into contact with a reagent for amplification.

Step f)

The DNA amplification in the amplification chambers AMP1, AMP2 is performed by standard amplification protocols of the prior art (typically any amplification method including but not limited to Polymerase Chain Reaction (PCR), Reverse transcriptase PCR and isothermal amplification) achieving a very good sensitivity and specificity up to 20 markers.

In each amplification chamber AMP1, AMP2, a separate set of primers have typically been immobilized during the manufacturing process. These primers are re-suspended when the amplification chambers AMP1, AMP2 are filled by a ready-to-use solution typically containing polymerase, nucleotides and reaction buffers at optimal concentrations for efficient amplification of DNA templates.

At the end of this step, one obtains an amplified DNA sample.

Step g)

In this step, the hybridization buffer contained in the functional volume V10 is transferred through the central hub CH to the two hybridization chambers (that can also be named detection chambers) HYB1, HYB2.

To this end, valve V10 is opened (all other valves V1 to V9 being closed) by the rotational-motion cam-driven actuator 1100 of the docking station 1000 and transferred to the central tube CT.

Then, valves V6 and V8 may successively be opened in order to proceed to the pre-filling of the hybridization chambers HYB1, HYB2 with the hybridization buffer if necessary.

Amplification chamber valves are opened and amplification solution is pushed to the hybridization chambers HYB1, HYB2.

The amplified DNA sample is then put into contact with hybridization buffer upon opening of the valves V13, V14 (which are typically independently actuated) into the hybridization chamber HYB1, HYB2 through the area-connecting micro-channels C13, C15B, C14, C16b connecting directly the two functional areas, namely the nucleic acid amplification area and the nucleic acid hybridization area.

Then, the valves V13, V14 are finally closed.

Step h)

In this step, the sample is placed into contact with the affinity sensor (e.g. the biochip) in such a way that the complementary sequences can be combined with an immobilized probe, for example by hybridization, association or linking to the probe. After the elimination of the non-associated material, the associated sequences are ready for detection and measurement.

Typically, in this step the amplified DNA sample is hybridized, during several minutes, e.g. about 30 minutes, in the hybridization chambers HYB1, HYB2. Recovering of the hybridized DNA is made by transferring the hybridization wash buffer contained in the functional volume T9 through the central hub CH to the hybridization chambers HYB1, HYB2. A hybridized DNA sample is therefore obtained.

In a variant of the analysis method, a DNA melting procedure at the end of hybridization may be added and would allow an increase in detection specificity.

Step i)

In this step, a microarray image is obtained and analyzed. It is noted that in accordance with the paragraph below, the hybridization chambers can therefore also be named detection chambers.

The detection of the interaction between the target nucleic acids and the probes are performed by an optical detection device. The localized hybridization is detected by the emission of a chromogenic signal. Herein, "chromogenic signal" is to be understood as any light signal emitted directly, or indirectly, after excitation by a suitable light source or after chemical or enzymatic transformation. Hence, are included in the category of the chromogenic signals, the colorimetric, photoluminescent, fluorescent, chemiluminescent, bioluminescent signals, or the like. Such signals are either directly emitted by the molecules of interest, or emitted by detectable elements (tags), which are added and/or grafted thereto.

A fluorescence reader can therefore allow obtaining a fluorescent image of the biochip surface. For that purpose, the biochip is illuminated with a light source at the wavelength of excitation of the fluorophore marking the target molecules, and an adapted optical system forms an image of the fluorescence of the biochip at the wavelength of emission of the fluorophores.

The light intensity of each point of this image is related to the quantity of fluorophores present at the corresponding point of the biochip, which is itself proportional to the number of target molecules that have been selectively attached at this place during the hybridization phase, which makes it possible to collect information (often quantitative) about the nucleic acid content of the sample. Detection of the signal is preferentially achieved by contact imaging forming a compact readout optical system as described for example in documents U.S. Pat. No. 7,306,766, FR2932885, US20050201899, PCT/FR2011/053208.

An automated analysis of the microarray image and a diagnostic report is then generated about the analysis of the biological sample.

Many different configurations are possible within the scope of this invention, including variations on part geometries, materials, methods of assemblies and configurations of parts relative to each other. The description above is meant to illustrate and represent one possible embodiment of the invention, and should not be construed to limit the possible scope of variations.

Figure 16:
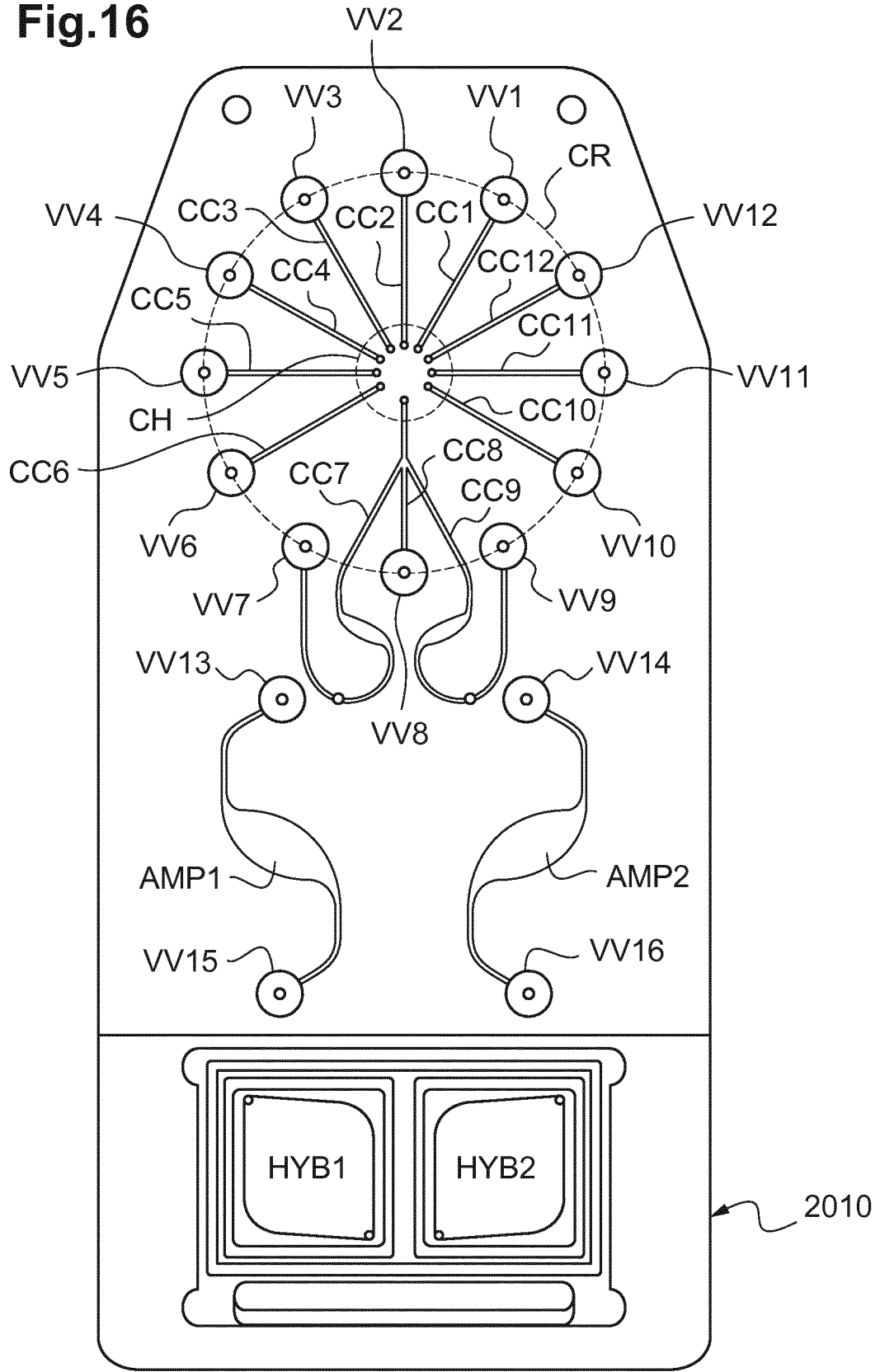
FIG. 16 is a detailed view of another example of cartridge plate.

For example, in the embodiment illustrated on FIG. 16, the microfluidic cartridge comprises a cartridge plate 2010.

The cartridge plate 2010 of the microfluidic cartridge comprises here a plurality of twelve valves VV1, VV2, VV3, VV4, VV4, VV5, VV6, VV7, VV8, VV9, VV10, VV1, VV12, each valve VV1, VV2, VV3, VV4, VV4, VV5, VV6, VV7, VV8, VV9, VV10, VV1, VV12 being located on a microchannel CC1, CC2, CC3, CC4, CC5, CC6, CC7, CC8, CC9, CC10, CC11, CC12 connected to the central distribution hub CH of fluids.

In this variant, all those twelve valves VV1, VV2, VV3, VV4, VV4, VV5, VV6, VV7, VV8, VV9, VV10, VV1, VV12 are arranged on a circle CR (see FIG. 16) on the cartridge plate 2010 in order to be actuated mechanically by an external cam-driven actuator.

The cartridge plate 2010 also comprises two couples of valves VV13, VV14, VV15, VV16 that may be actuated by independent linear actuators in order to transfer fluids, for example, from the sample preparation area to the nucleic acid amplification area AMP1, AMP2 and the nucleic acid analysis area HYB1, HYB2.

Typically in this embodiment, the cartridge comprises metering chambers that are located between the central HUB and each amplification chamber. Said metering chambers can be connected to the said amplification chambers through valves VV8 and VV14. Typically said metering chambers are also connected to the central HUB. Additionally, said metering chambers can also be directly connected, through a microchannel, to a valve of a hub-connected microchannel (for example valves VV9 and VV7).

The person skilled in the art would adapt other elements of the microfluidic cartridge, e.g. the cartridge body and the cartridge cover, in order to adapt the cartridge plate 2010 to the different functional volumes of the microfluidic cartridge.

The invention claimed is:

1. A microfluidic cartridge configured to detect at least one nucleic acid of a sample, the microfluidic cartridge comprising:
a cartridge plate comprising a substrate having a first face and a second face;
a cartridge body connected with the cartridge plate at the second face of the substrate of the cartridge plate;
one central distribution hub configured to pump, inject, and distribute fluids, the central distribution hub comprising a hub body disposed within the cartridge body and connected to the cartridge plate, the central distribution hub being configured to be connected to a system providing pressure or depressurization within the hub body to pump, inject and distribute fluids;
a plurality of chambers defined within the cartridge body or within the cartridge plate and configured to hold fluids;
a network of fluidic microchannels formed in the cartridge plate and comprising at least three hub-connected microchannels connected with the one central distribution hub, a first set of chambers of the plurality of chambers being fluidly connected to the one central distribution hub by a corresponding one of the hub-connected microchannels, the central distribution hub being configured to pump and inject the fluids from at least one chamber of the first set of chambers to at least one other chamber of the first set of chambers; and
a plurality of valves each located on a respective one of the fluidic microchannels, each of the valves comprising a deformable membrane and a valve seat formed by a recess in the cartridge plate opposite the deformable membrane, the deformable membranes being configured to deform in relation to the cartridge plate to control distribution of the fluids between at least the first set of chambers.

2. The microfluidic cartridge according to claim 1, wherein the first set of chambers is arranged around the central distribution hub.

3. The microfluidic cartridge according to claim 1, wherein the network of fluidic microchannels further comprises non-hub-connected microchannels connecting at least one chamber of the plurality of chambers to at least one other chamber of the plurality of chambers.

4. The microfluidic cartridge according to claim 3, wherein the deformable membranes are configured to deform in relation to the cartridge plate to control distribution of the fluids between the first set of chambers and a second set of chambers of the plurality of chambers connected to the non-hub-connected microchannels.

5. The microfluidic cartridge according to claim 3, wherein the deformable membranes are configured to deform in relation to the cartridge plate to control distribution of the fluids between a second set of chambers of the plurality of chambers to one another, the second set of chambers being connected to the non-hub-connected microchannels.

6. The microfluidic cartridge according to claim 1, wherein two chambers of a second set of chambers of the plurality of chambers are directly fluidly connected to each other by one or more non-hub-connecting microchannels.

7. The microfluidic cartridge according to claim 1, wherein at least three of the valves are circularly arranged in the microfluidic cartridge.

8. The microfluidic cartridge according to claim 1, wherein a set of the valves are linearly arranged in the microfluidic cartridge.

9. The microfluidic cartridge according to claim 1, wherein each of the hub-connected microchannels comprises one of the valves located at a chamber end of the respective hub-connected microchannel.

10. The microfluidic cartridge according to claim 1, comprising a cartridge cover configured to close the first set of chambers, and wherein the cartridge plate comprises:
a plurality of grooves flush with the first face or the second face of the substrate and a plurality of through holes connecting the first face and the second face, and
a first film bonded on the first face of the substrate of the cartridge plate, the grooves flush with the first face being sealed by the first film to form the hub-connected microchannels, the first film being one of the deformable membranes configured to be deformed by an external actuator,
wherein the cartridge body comprises:
a lateral wall which extends from the second face of the substrate, and
a plurality of internal walls which define chambers of the first set of chambers.

11. The microfluidic cartridge according to claim 10, further comprising a semi-permeable membrane between the cartridge body and the cartridge cover configured to let air pass therethrough while preventing liquids from leaking out of the first set of chambers.

12. The microfluidic cartridge according to claim 10, wherein the cartridge plate comprises a second film bonded on the second face of the substrate of the cartridge plate, the plurality of grooves flush with the second face being sealed by the second film to form non-hub-connected microchannels.

13. The microfluidic cartridge according to claim 10, further comprising a plurality of recessed cavities formed in the cartridge plate, the recessed cavities being made in the first face of the substate and extending from the first face toward the inside of the substrate.

14. The microfluidic cartridge according to claim 1, wherein the cartridge plate comprises
at least one recessed cavity formed in the substrate and extending from the first face, and
a microarray slide bonded on the first face of the substrate closing the at least one recessed cavity to form at least one detection chamber of a second set of chambers of the plurality of chambers for nucleic acid analysis.

15. The microfluidic cartridge according to claim 1, wherein each of one or more chambers the first set of chambers of the plurality of chambers is configured to receive a tube containing a sample, reagent products, or a purification column.

16. The microfluidic cartridge according to claim 1, wherein the central distribution hub comprises a plunger seal configured to slide in and out of the hub body to pump from or inject fluids in the chambers through the hub-connected microchannels.

17. The microfluidic cartridge according to claim 16, wherein the central distribution hub comprises a syringe having a plunger to which the plunger seal is attached.

18. A microfluidic cartridge system comprising:
a microfluidic cartridge configured to detect at least one nucleic acid of a sample, the microfluidic cartridge comprising:
a cartridge plate comprising a substrate having a first face and a second face,
a cartridge body connected with the cartridge plate at the second face of the substrate of the cartridge plate,
one central distribution hub configured to pump, inject, and distribute fluids, the central distribution hub comprising a hub body disposed within the cartridge body and connected to the cartridge plate, the central distribution hub being configured to be connected to a system providing pressure or depressurization within the hub body to pump, inject and distribute fluids,
a plurality of chambers defined within the cartridge body or within the cartridge plate and configured to hold fluids,
a network of fluidic microchannels formed in the cartridge plate and comprising at least three hub-connected microchannels connected with the one central distribution hub, each chamber of a first set of chambers of the plurality of chambers being fluidly connected to the one central distribution hub by a corresponding one of the hub-connected microchannels, the central distribution hub being configured to pump and inject the fluids from at least one of the first set of chambers to at least another of the first set of chambers, and
a plurality of valves each located on a respective one of the fluidic microchannels, each of the valves comprising a deformable membrane and a valve seat formed by a recess in the cartridge plate opposite the deformable membrane, the deformable membranes being configured to deform in relation to the cartridge plate to control distribution of the fluids between at least the first set of chambers; and
a docking station configured to receive the microfluidic cartridge, the docking station comprising a cam-driven actuator configured to mechanically actuate the valves of the hub-connected microchannels.

19. The microfluidic cartridge system according to claim 18, wherein the microfluidic cartridge further comprises a microarray slide, and
the docking station further comprises:
an optical exciter configured to excite the microarray slide of the microfluidic cartridge,
an optical detector configured to optically detect an optical signal that is representative of said nucleic acid in the sample analyzed by the microfluidic cartridge, and
an actuator configured to actuate the valves.

20. The microfluidic cartridge system according to claim 19, wherein the docking system further comprises a contact imaging device forming a compact readout optical system for detection of a presence of nucleic acids analyzed in the microfluidic cartridge.

* * * * *

UNITED STATES PATENT AND TRADEMARK OFFICE
CERTIFICATE OF CORRECTION

PATENT NO. : 12,275,009 B2
APPLICATION NO. : 18/482796
DATED : April 15, 2025
INVENTOR(S) : Yann Marcy et al.

It is certified that error appears in the above-identified patent and that said Letters Patent is hereby corrected as shown below:

On the Title Page

In Item (72), under "Inventors", in Column 1, Line 2, delete "Noisy Sur Ecole" and insert -- Noisy-sur-École --, therefor.

In the Specification

In Column 1, Line 10, delete "'371" and insert -- 371 --, therefor.

In Column 3, Line 27, delete "theses" and insert -- these --, therefor.

In Column 6, Line 56, delete "sample §.," and insert -- sample S, --, therefor.

In Column 7, Line 9, delete "by" and insert -- be --, therefor.

In Column 7, Lines 11-12, delete "polydimetyl-siloxane" and insert -- polydimethyl-siloxane --, therefor.

In Column 7, Line 53, delete "valves" and insert -- valves, --, therefor.

In Column 8, Line 14, delete "to" and insert -- as to --, therefor.

In Column 9, Line 42, delete "H1c à" and insert -- H1c, --, therefor.

In Column 11, Line 27, delete "hybridizations" and insert -- hybridization --, therefor.

In Column 11, Line 66, delete "polydimetyl-siloxane" and insert -- polydimethyl-siloxane --, therefor.

Signed and Sealed this
Nineteenth Day of August, 2025

Coke Morgan Stewart
*Acting Director of the United States Patent and Trademark Office*